(12) United States Patent
Pierer et al.

(10) Patent No.: US 6,340,362 B1
(45) Date of Patent: Jan. 22, 2002

(54) PLATE FOR JOINING A PELVIC FRACTURE

(75) Inventors: Wolfgang Pierer, Chemnitz; Hubert Zeidler, Neukirchen, both of (DE)

(73) Assignee: IMPAQ GmbH Medizintechnik, Lauterbach-Sulzbach (DE)

( * ) Notice: Subject to any disclaimer, the term of this patent is extended or adjusted under 35 U.S.C. 154(b) by 0 days.

(21) Appl. No.: 09/619,031

(22) Filed: Jul. 19, 2000

Related U.S. Application Data

(63) Continuation of application No. PCT/EP99/00374, filed on Jan. 21, 1999.

(30) Foreign Application Priority Data

Jan. 22, 1998 (DE) .......................................... 198 02 229

(51) Int. Cl.[7] .............................................. A61B 17/80
(52) U.S. Cl. ...................................................... 606/71
(58) Field of Search ............................. 606/53, 61, 69, 606/70, 71, 54, 55, 60

(56) References Cited

U.S. PATENT DOCUMENTS

| | | |
|---|---|---|
| 4,454,876 A | 6/1984 | Mears |
| 4,573,458 A | 3/1986 | Lower |
| 5,643,267 A | 7/1997 | Hitomi et al. |
| 6,001,103 A | 12/1999 | Hitomi et al. |

FOREIGN PATENT DOCUMENTS

| | | |
|---|---|---|
| DE | 2603087 B1 | 6/1977 |
| DE | 3043566 A1 | 7/1982 |
| DE | 4307540 A1 | 9/1993 |
| DE | 19808229 C2 | 9/1999 |
| WO | WO-82/01645 A1 * | 5/1982 |

OTHER PUBLICATIONS

PCT Application No. PCT/EP99/00374, filed Jan. 21, 1999.

* cited by examiner

*Primary Examiner*—David O. Reip
(74) *Attorney, Agent, or Firm*—Harness, Dickey & Pierce, P.L.C.

(57) ABSTRACT

A plate is provided for joining a fracture of the pelvis. The plate is securable on either side of the fracture by fasteners to the pelvic bone portions to be connected. The plate is formed of at least two parts arranged along an axial direction. A first engaging portion is provided on one part for connecting the parts, which engages with a second engaging portion provided on the other part, such that the two parts are secured to one another in an axial direction and in a transverse direction to the plate plane. The two parts may undergo limited pivotal movement relative to one another.

12 Claims, 4 Drawing Sheets

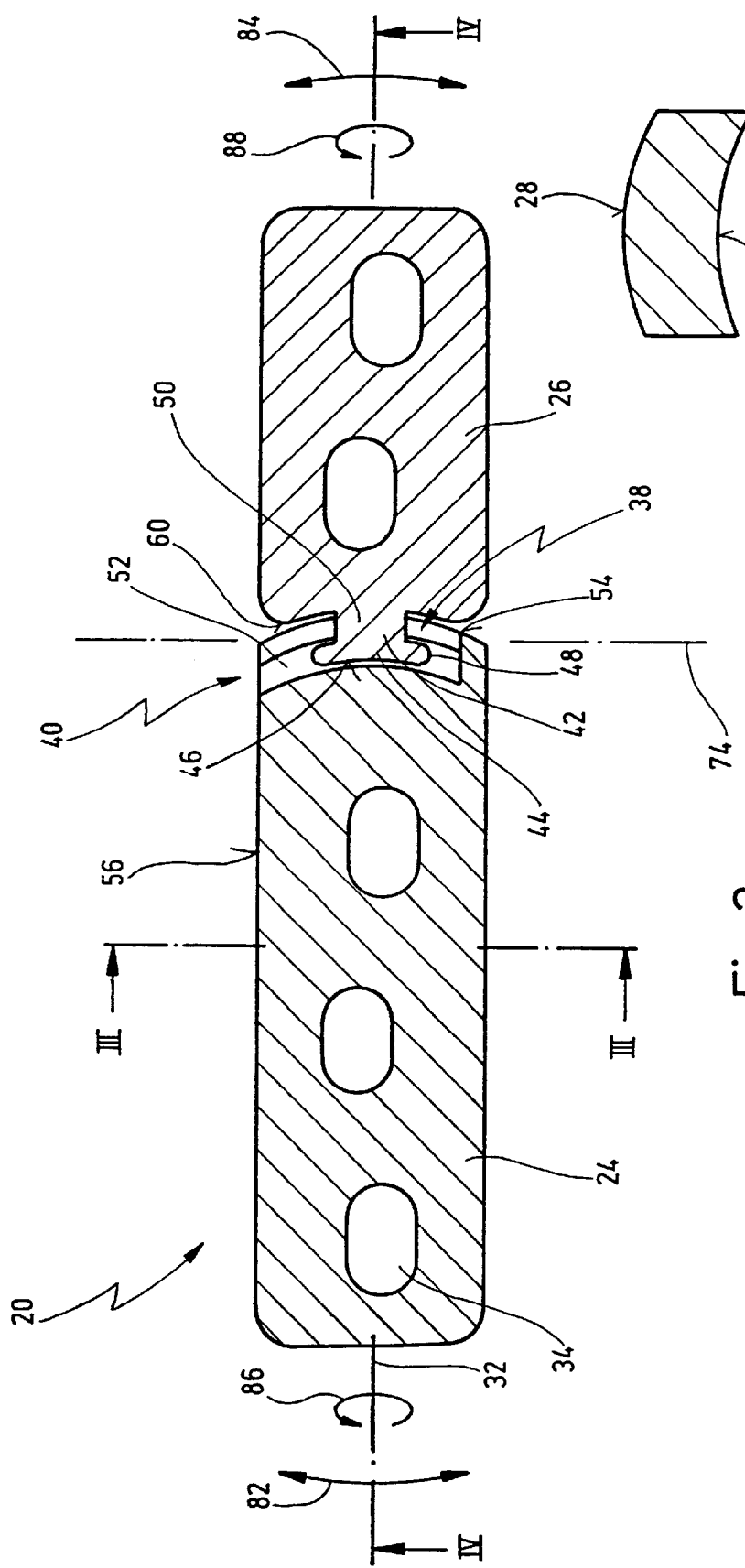

PLATE FOR JOINING A PELVIC FRACTURE

CROSS REFERENCE TO PENDING APPLICATION

The present application is a continuaton of pending International patent application PCT/EP 99/00374 filed Jan. 21, 1999.

BACKGROUND OF THE INVENTION

The invention relates to a plate for joining a pelvic fracture, wherein the plate can be fastened by fastening means like screws, nails or the like on either side of said facture to pelvic bone portions to be connected.

Such a plate is known from German patent DE 2 603 087. If a fracture of the pelvis has occured, a plate is fastened to the pelvic for osteosynthesis, i.e. to aid healing of the broken pelvic bone. The plate is placed approximately transversly to the fracture and is fixed to the two portions of the pelvic bone to be connected on either side of the fracture.

The conventional plates are integrally formed as rigid plates, which are secured by means of screws, nails or the like to the bone portions.

The rigid plates, usually made of refined steel, have however drawbacks. The bone portions on either side of the fracture are rigidly fixed to one another with respect to all degrees of freedom. No consideration is made of the fact that the pelvis does not represent a rigid bone system. Rather, the anatomy of the pelvis provides several bone sections, which allow relative movement to one another. In particular, the lower left and right pelvic bones in the region of the coccyx, the pubic arches (arci pubici), are only connected to one another by cartilage, i.e. by the pubic symphysis (symphysis pubica). The cartilage connection between the pubic arches acts as a pivot connection, which allows relative movement of the arches during various human activities, for example walking, lying down or sitting.

A fracture of this cartilage is normally vertical. A plate is spanned across the cartilage transversly to the fracture direction and is fastened to the pubic arches on either side of the cartilage. The fractured cartilage is allowed to heal by holding the two arches together by means of the plate. The conventional rigid plate guarantees support of the two arches, however due to its rigid construction, the plate prevents all other natural movements of the two pelvic bone portions relative to one another, as is the case with the plate known from DE 26 03 087 mentioned above.

The afore-mentioned known plate for fixing a symphysis fracture comprises a plate made of plastics comprising an overall homogenous thickness. The plate is bent in form of a collar comprising two unconnected side parts at its rear side and a front part prolongated over the side parts downwardly and having a central indentation at its rim. The rearward rims of the side parts are tilted relative to each other and rolled round so far that they run parallel to the front side plate plane in an transition region between the front part and the side parts.

Movement of the patient in bed, for example when the patient turns from his back over to his side, causes torques and tensile forces to be exerted on the two lower pelvic bone portions. These forces are transferred to the plate and the screws and nails, because the conventional rigid plate does not allow relative movement of the bone portions. The forces are great enough that they could tear out the screws or nails. When using such conventional plates, the patient must therefore be completely immobilized to avoid pulling out the screws or nails, which, however, is unpleasant for the patient.

The object of the present invention is to provide an improved plate of the mentioned type, where the patient with a pelvic fracture can move without the screws or nails securing the plate to the pelvic bone being torn out and where at the same time it is guaranteed that the pelvic fracture is securely held and can heal.

SUMMARY OF THE INVENTION

According to the present invention, the object underlying the invention is achieved by a plate of the kind mentioned at the outset, comprising:

at least two parts arranged along an axial direction of said plate, a first engaging means provided on one of said parts, second engaging means provided on the other of said parts, wherein said first engaging means and said second engaging means are intended to connect said two parts with each other, and wherein said first and second engaging means are formed such that said two parts are secured to one another in said axial direction and in a transverse direction to a plate plane, and that said two parts are moveable relative to one another in a limited pivotal range.

The two-part configuration of the plate has the advantage over the conventional one-piece rigid configuration that relative motion is allowed between the interconnected pelvic bone portions. Through the interconnection of the two parts with the two engaging means, the two parts are secured to one another in axial direction and in transverse direction to the plate plane, such that the fracture is securely supported transversely to the fracture direction. Thus healing of the fracture is guaranteed, because the engaging means prevent the two pelvic bone portions on either side of the fracture from moving apart.

By providing the two parts to be moveable relative to one another by a certain limited pivotal movement, the advantage is achieved that the bone portions interconnected by the plate can maintain their natural, anatomical relative movement. It is also avoided that the bone screws or nails are torn out of the pelvic bone portions when the patient moves. The plate according to the present invention provides a degree of freedom of relative movement of the two parts within a limited angular range. The limited relative motion of the two parts can be achieved for example in that the engaging means interact with play therebetween.

In a preferred embodiment, the two parts have a limited pivotal movement about a first pivot axis running transversly to the plate plane.

This feature allows the two parts to rotate or pivot by a limited amount relative to one another in the plate plane. The advantage is achieved that the natural movement of the pubic arches is maintained, for example when the patient is standing up and one leg carries more weight than the other.

In a further preferred embodiment, the two parts have a limited pivotal movement about a second pivot axis running in the plate plane transversely to the axial direction.

This allows the two parts to be rotated with respect to one another out of the plate plane. The advantage is achieved that the relative movement of the pubic arches is also maintained, for example when the patient turns over in bed or rises to a sitting position.

In a further preferred embodiment, the two parts are counter-directionally rotatable with respect to one another about the longitudinal axis by a limited angle.

This feature of the plate according to the invention provides the advantage of a further degree of freedom of the relative motion.

In a further preferred embodiment the first engaging means comprises at least one surface oriented substantially transversely to the plate plane and transversely to the axial direction which engages behind a surface of the second engaging means oriented substantially transversely to the plate plane and transversely to the axial direction, and wherein two surfaces are arranged to have play there between.

The two counter-engaging surfaces on the two engaging means engaging behind each other ensure that the two parts of the plate according to the present invention are secured against tensile forces in the axial direction and in transverse direction to the plate plane. In this manner, a mechanically simple connection of the two parts of the plate is advantageously provided. The orientation of the two surfaces can be perpendicular to the plate plane and perpendicular to the axial direction, wherein in this case, two additional overlying engagement surfaces are necessary. These additional surfaces have an orientation approximately parallel to the plate plane, for example in the form of engagement means formed as back cuts to secure the two parts in transverse direction to the plate plane. However, it is more advantageous that the two surfaces are oriented such that they have both a component perpendicular to the plate plane and also a component parallel to the plate plane, so that a securement of the parts in axial direction and in transverse direction to the plate plane is simultaneously guaranteed. Since the surfaces engage one another with a certain play, a degree of freedom of pivot within a limited angular range is provided with particularly simple mechanical means.

Preferably, one end face of one part is formed to be convex in the plate plane and an end face of the other opposing part is correspondingly formed to be concave.

With this configuration of the two opposing end faces of the parts being connected, it is avoided that the two parts block or catch with one another during the relative movement. In addition, the configuration of the end faces allows the two parts to be secured to one another on the pelvis not only in a straight line configuration, but depending on the given anatomy, at an angular disposition with respect to one another.

In a preferred embodiment, the first engaging means comprise a projection formed at one end of the one part and the second engaging means comprise a recess formed at one end of the other part, wherein the projection engages the recess with play therebetween.

With this configuration of the two engaging means of the plate according to the present invention, a connection of the two parts is formed in a mechanically simple manner.

Preferably, the projection has a substantially T-shaped cross section and the recess has a substantially C-shaped cross section.

This provides an advantageously simple construction, where the two parts are secured against tensile forces acting in axial direction and in transverse direction and where on the other hand, a pivotal motion of the two parts relative to one another is allowed.

Preferably, a front portion of the projection extends in the plate plane transversely to the axial direction.

Since the plate generally has a greater width than thickness, this feature has the advantage that the front portion which forms the cross bar of the T-shaped cross section can extend over the entire width of the plate and therefore provides greater stability.

In addition, it is preferred that the recess be laterally open.

The side opening of the recess has the advantage that the other part of the plate according to the present invention with the T-shaped projection can be inserted in the recess from the side. Thus, when not mounted on the pelvis, the plate according to the present invention can be disassembled into its two parts. Since such plates are intended for multiple use, the further advantage is achieved that the two parts can be easily cleaned for example in an autoclave.

In conjunction with the curved formation of the end faces of the two parts, the recess is preferably provided to extend over the entire width of the one part. The advantage is achieved that the two parts can be secured to the pelvic bone portions at a predetermined angular position with respect to the pivot axis transversly to the axial direction and transversly to the plate plane. The relative movement of the part about the pivot axis or pivot axes then takes place about this angular position defined by the mounting on the pelvis. This angular position can be adjusted in a relatively wide angular range, which allows better adaptation of the present plate to the given anatomical situation or to the given fracture direction. The two parts obviously cannot be disassembled when mounted on the pelvis.

In a further preferred embodiment, the recess comprises a backside formed to be convex.

With this feature, the T-shaped projection engaging the recess cannot catch or be blocked in the recess. Advantageously, the functional reliability of the present plate is improved.

In a further preferred embodiment, the first engaging means and the second engaging means are formed in dovetail shape.

This has the advantage that the two parts of the plate according to the present invention in the region of the engaging means can be formed to be stronger and carry higher mechanical load. A further advantage of this configuration of the engaging means is that the two parts can be formed identically and thus the production costs of the plate according to the present invention can be reduced.

In a further preferred embodiment, the plate is made of titanium.

The advantage is a plate of reduced weight, which at the same time has high tensile and compression properties as well as high break resistance. Preferably, the two parts of the plate are formed by casting, where then the engaging means can be formed as one piece with the parts of the plate.

Further advantages will become apparent from the following description together with the appended drawings. It will be understood that the above-mentioned features and those to be discussed below are not limited to the given combinations, but may be employed in other combinations or taken alone, without departing from the scope of the present invention. Embodiments of the invention are illustrated in the drawings and will be discussed below.

BRIEF DESCRIPTION OF THE DRAWINGS

FIG. 2 shows a longitudinal cross section through the plate of FIG. 1 in the plate plane along the line II—II in FIG. 4.

FIG. 3 shows a cross section of the plate along the line III—III in FIG. 2.

DETAILED DESCRIPTION OF PREFERRED EMBODIMENTS

Figure 1:
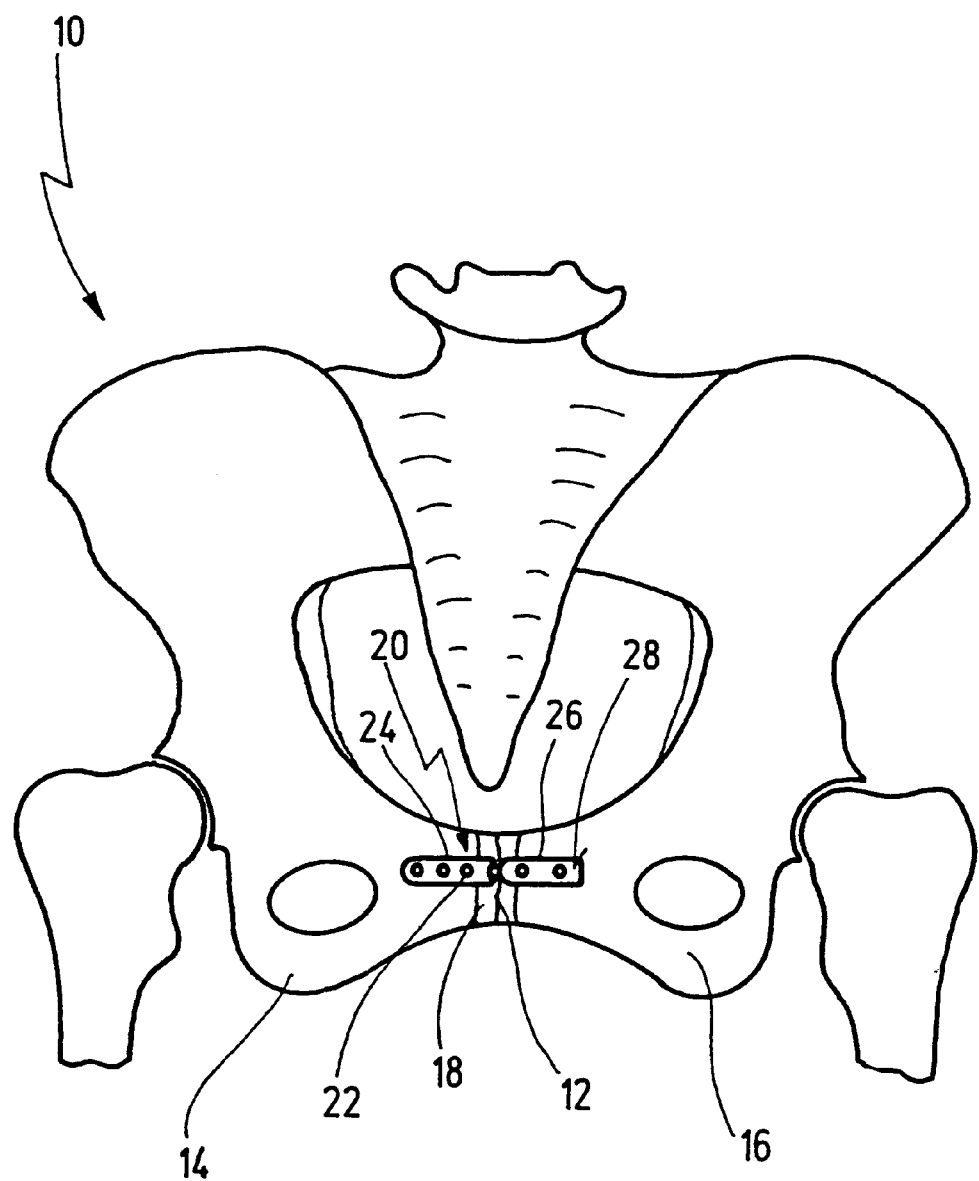
FIG. 1 shows a back view of a pelvis having a plate secured thereto for joining a fracture of the pelvis.

A pelvis 10 of the human skeleton is illustrated in FIG. 1. A fracture 12 is present in pelvis 10, which was caused by an external force, for example through an accident. A pelvic bone portion 14 is shown to the left of fracture 12, the left pubic arch. A further pelvic bone portion 16 is located to the right of fracture 12, the right pubic arch. Left and right bone portions 14, 16 are connected to one another by cartilage, i.e. the pubic symphysis 18.

Symphysis 18 allows relative movement of the bone portions 14 and 16, namely in the form of a pivot joint with limited degrees of freedom. Bone portions 14, 16 can rotate or pivot for example about symphysis 18 as a pivot axis. Portions 14 and 16 are shiftable with respect to one another in vertical direction or can also rotate about an imaginary axis running transversly to symphysis 18.

Fracture 12 shown in FIG. 1 represents the case of a crack in symphysis 18, which runs vertically in symphysis 18. In order to join fracture 12, a plate 20 is secured to pelvic bone portions 14, 16 by means of screws or nails 22, plate 20 being placed in transverse direction to fracture 12. Screws or nails 22 are directly screwed into or hammered into bone portions 14 and 16.

Plate 20 will be explained in more detail with reference to FIGS. 2 to 4. Plate 20 is formed of two parts 24 and 26, which are provided in the form of plate-shaped elements. Furthermore, the two parts 24, 26 are made of titanium, preferably produced as casted elements. An upper side 28 and an underside 30 of parts 24, 26 are curved to be convex and concave, respectively. Parts 24, 26 are mounted to pelvis 10 at their respective undersides 30. Depending on the anatomy, the two parts 24, 26 however could also be formed with the upper and lower sides having different shapes.

Part 24 of plate 20 in this embodiment is longer than part 26, which however is understood here only as one possible selection of the dimensions of parts 24, 26. The dimensions will generally depend on the given anatomy.

The two parts 24, 26 of plate 20 are arranged adjacent to one another in the axial direction of plate 20, i.e. along a longitudinal axis 32 and are connected to one another. The connecting point of the two parts 24, 26 is located above fracture 12 when plate 20 is secured to pelvis 10. The two parts 24, 26 comprise bore holes 34 in the form of slatted holes, through which screws or nails 22 are passed for securing parts 24, 26 to pubic bone portions 14, 16. Three holes 34 are provided in part 24 and two holes 34 in part 26. As can be seen in FIG. 4, holes 34 expand toward upper side 28, so that heads of the screws or nails 22 sink in the expanded portions of bore holes 34.

First engaging means 38 are provided on part 26, which engages for connection with second engaging means 40 provided on part 24. First engaging means 38 include a projection 42 with T-shaped cross section. Projection 42 is integrally formed in one piece with part 26. A front portion 44 of projection 42 extends laterally to the axial direction of plate 20 in the plane of the plate as shown in FIG. 2, i.e. transversly to longitudinal axis 32. A front side 46 of front portion 44 is slightly concave. Side ends 48 of the front portion 44 are rounded. Front portion 44 connects with the remaining body of part 26 via a bridge 50 extending in the axial direction of plate 20.

Second engaging means 40 of part 24 include a recess 52 having a C-shaped cross section. At a front end 54, recess 52 opens in the form of a slot, which in transverse direction to the plate plane has an opening width which is smaller than the remaining hollow space of recess 52. In addition, recess 52 is open toward one side 56 of part 24.

A backside 58 of recess 52 is formed to be convex in the form of a hump.

When parts 24, 26 of plate 20 are not secured to pelvis 10, part 26 can be removed from part 24 by removing projection 42 of part 26 out of recess 52 from the side. Conversely, parts 24, 26 can be reassembled by inserting projection 42 from the side into recess 52.

End face 54 of part 24 is formed to be convex in the plate plane. Correspondingly, an end face 60 of part 26 opposing end face 54, is formed to be concave. Recess 52 and front portion 44 of projection 42 are also curved in the plate plane.

Recess 52 comprises a surface 62 oriented transversly to the plate plane and transversly to the axial direction, which engages a surface 64 of front portion 44 of projection 42, also oriented transversly to the plate plane and transversly to the axial direction. The same holds for a surface 66 of the projection 42, which engages a surface 68 of recess 52. The two parts 24, 26 are thus secured to one another in the direction of a double arrow 70, i.e. in axial direction of plate 20, through counter-engaging surfaces 62, 64 and 66, 68. Since projection 42 is partially enclosed in recess 52, parts 24, 26 are also secured to one another in the direction of a double arrow 72, i.e. transversely to the plate plane. Surfaces 62, 64 and 66, 68 are disposed to have play therebetween.

Projection 42 is disposed with play in recess 52, which allows pivotal movement of parts 24, 26 with respect to one another in a limited angular region. In FIG. 2, a pivot axis 74 is shown lying in the plate plane and running transversely to the axial direction of plate 20, about which parts 24, 26 can be rotated as shown by double arrows 76, 78. The pivot movement about axis 74 is limited to an angular range of about 0° to 5°. The pivotal movement is limited, because end faces 54 and 60 hit one another at a certain rotation and therefore limit the pivotal movement. The pivotal movement however is also limited by the play between projection 42 and recess 52.

Figure 4:
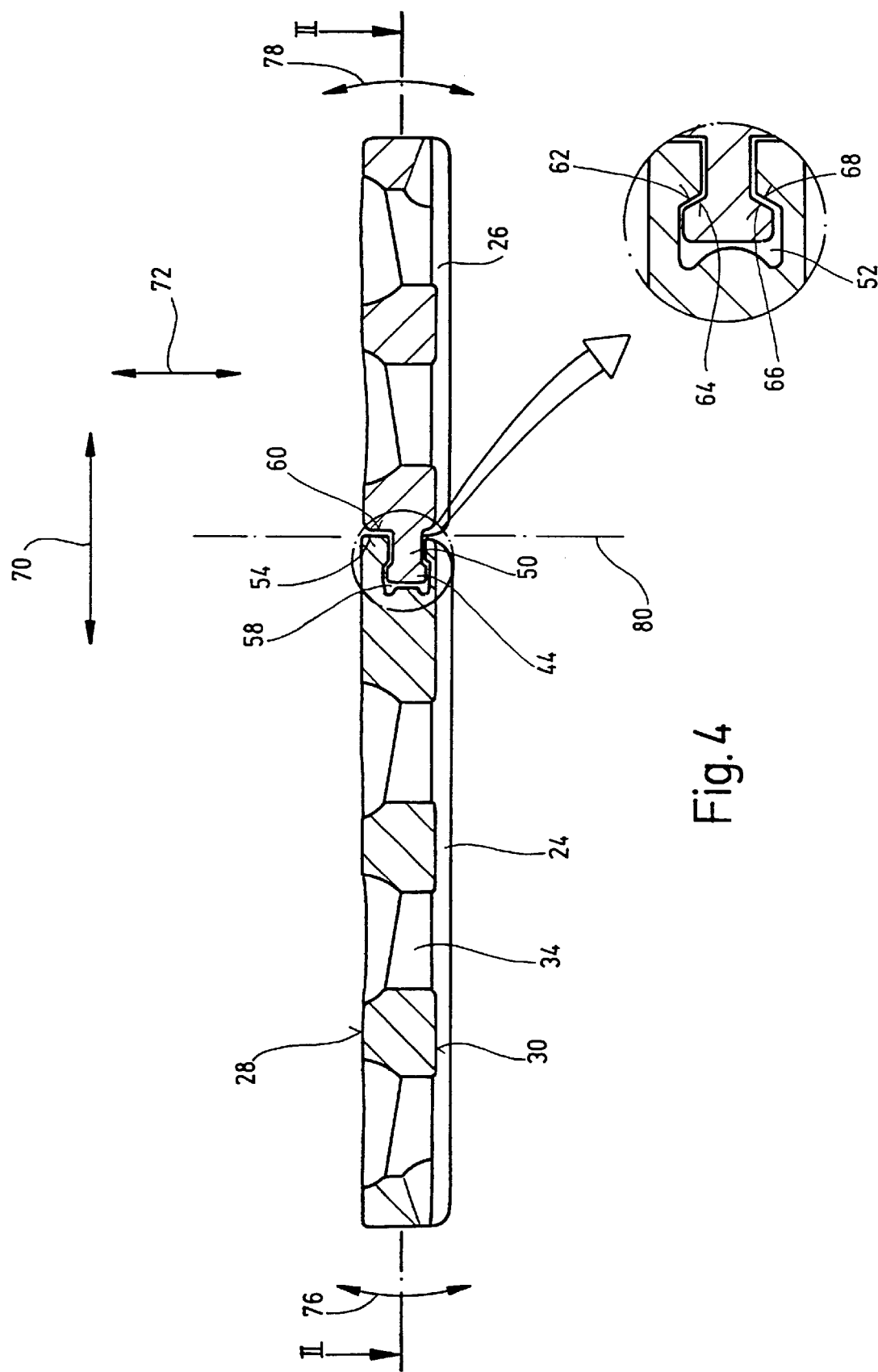
FIG. 4 shows a longitudinal cross section through the plate along the line IV—IV in FIG. 2.

Furthermore, a pivot axis 80 is shown in FIG. 4 running transversely to the plate plane and transversely to the axial direction of plate 20, about which the two parts 24, 26 are pivotal relative to one another as indicated by double arrows 82, 84 in FIG. 2. The pivotal movement about pivot axis 80 is also limited by the hitting of end faces 54, 60 of parts 24, 26. The pivotal movement about pivot axis 80 may also be in an angular range of 0° to 5°.

Although parts 24, 26 in FIG. 1 are arranged along a line, it is also possible to mount parts 24, 26 to the pelvis, if necessary, at a certain angular position relative to one another about pivot axis 80. This angular position can be adjusted by placing projection 42 further into recess 52 or further out of recess 52 as compared to the central positioning shown in FIG. 2.

Finally, the play between projection 42 and recess 52 allows a counter-directional rotation of parts 24, 26 about longitudinal axis 32 in a limited angular range of about 0° to 5°, as shown by the arrows 86 and 88 in FIG. 2.

Figure 5:
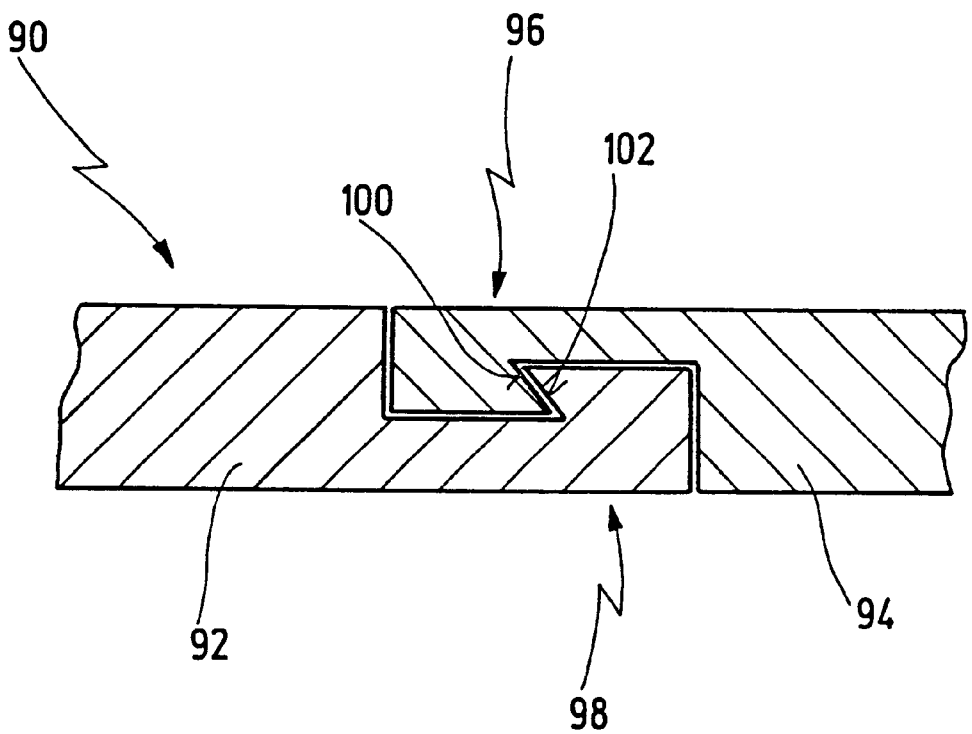
FIG. 5 shows a partial view of a second embodiment of the plate in a longitudinal cross section as in FIG. 4.
Figure 6:
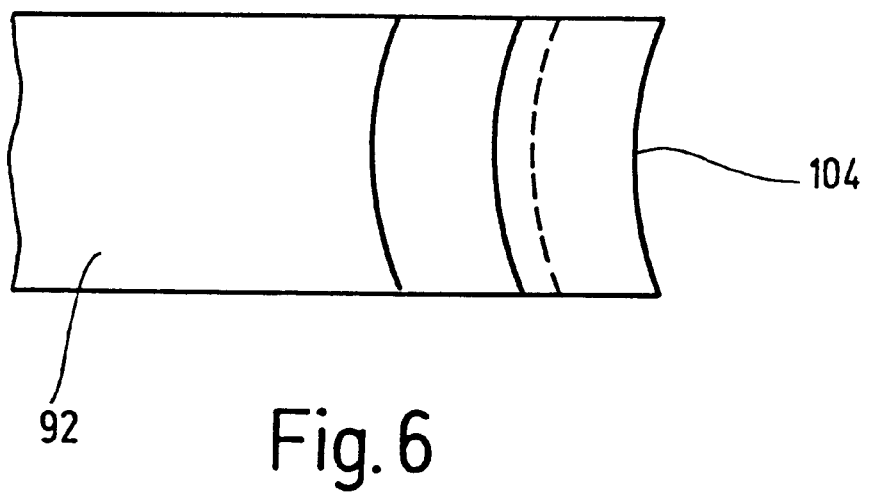
FIG. 6 shows a plan view of one part of the plate in FIG. 5.

A second embodiment of a plate 90 is shown in FIGS. 5 and 6, which is formed of a part 92 and a part 94. The two parts 92, 94 are identical. Part 94 of plate 90 comprises first engaging means 96, which engage with a second engaging means 98 of part 92. First engaging means 96 and second engaging means 98 form a dovetail-like connection of the two parts 92, 94. First engaging means 96 comprise a surface 100 running transversly to the axial direction of plate 90 and transversly to the plate plane. This surface engages an approximately similarly oriented surface 102 of the second engaging means 98 of part 92. Surfaces 100 and 102 are formed by back cuttings on parts 92, 94 of plate 90.

Surfaces 100 and 102 secure parts 92, 94 in both the axial direction of plate 90 and also in transverse direction to the plate plane. The adjoining surfaces of parts 92, 94 also have play therebetween, to allow parts 92, 94 to be connected to one another with a limited relative movement. In addition, an end face 104 of part 92 is formed to be concave, where the end face of part 94, opposing the end face 104, is correspondingly formed to be convex. On the whole, the function of plate 90 corresponds to the function of plate 20.

What is claimed is:

1. A plate for joining a fracture of the pelvis, wherein said plate can be fastened on either side of said fracture by means of fastening means to pelvic bone portions to be connected, said plate comprising:

at least two parts arranged along an axial direction of said plate, a first engaging means provided on one of said parts, second engaging means provided on the other of said parts, wherein said first engaging means and said second engaging means are intended to connect said two parts with each other, and wherein said first and second engaging means are formed such that said two parts are secured to one another in said axial direction and in a transverse direction to a plate plane, and that said two parts are moveable relative to one another in a limited pivotal range about said axial direction.

2. The plate of claim 1, wherein said parts have a limited pivotal movement about a first pivot axis running transversely to said plate plane.

3. The plate of claim 1, wherein said parts have a limited pivotal movement about a second pivot axis running in said plate plane transversely to said axial direction.

4. The plate of claim 1, wherein said first engaging means comprises at least one surface oriented substantially transversely to said plate plane and transversely to said axial direction, which engages behind a surface of the second engaging means oriented substantially transversely to said plate plane and transversely to said axial direction and wherein said surfaces are arranged to have play therebetween.

5. The plate of claim 1, wherein an end face of one of said parts is formed to be convex and an opposing end face of the other part is formed to be concave.

6. The plate of claim 1, wherein said first engaging means comprise a projection formed at one end of the one of said parts and said second engaging means comprise a recess formed at one end of the other of said parts, wherein said projection engages said recess with play therebetween.

7. The plate of claim 6, wherein said projection has a substantially T-shaped cross section and said recess has a substantially C-shaped cross section.

8. The plate of claim 7, wherein a front portion of said projection extends in said plate plane transversely to said axial direction.

9. The plate of claim 1, wherein said first engaging means comprise a projection formed at one end of the one of said parts and said second engaging means comprise a recess formed at one end of the other of said parts, wherein said projection engages said recess with play therebetween and wherein said recess is laterally open.

10. The plate of claim 1, wherein said first engaging means comprise a projection formed at one end of the one of said parts and said second engaging means comprise a recess formed at one end of the other of said parts, wherein said projection engages said recess with play therebetween and wherein said recess is formed to be convex at a backside.

11. The plate of claim 1, wherein said first engaging means and said second engaging means are formed in dovetail shape.

12. The plate of claim 1, wherein said plate is made of titanium.

* * * * *

UNITED STATES PATENT AND TRADEMARK OFFICE
CERTIFICATE OF CORRECTION

PATENT NO.    : 6,340,362 B1
DATED         : January 22, 2002
INVENTOR(S)   : Wolfgang Pierer et al.

It is certified that error appears in the above-identified patent and that said Letters Patent is hereby corrected as shown below:

<u>Title page,</u>
Item "[73], Assignee:", "IMPAQ" should be -- IMPAG --.

Signed and Sealed this

Third Day of September, 2002

*Attest:*

*Attesting Officer*

JAMES E. ROGAN
*Director of the United States Patent and Trademark Office*